United States Patent [19]

Karanewsky

[11] Patent Number: 5,102,875

[45] Date of Patent: Apr. 7, 1992

[54] PHOSPHONATE SUBSTITUTED AMINO ACIDS USEFUL AS ANTIHYPERTENSIVES

[75] Inventor: Donald S. Karanewsky, West Windsor, N.J.

[73] Assignee: E. R. Squibb & Sons, Inc., Princeton, N.J.

[21] Appl. No.: 542,504

[22] Filed: Jun. 25, 1990

Related U.S. Application Data

[62] Division of Ser. No. 396,170, Aug. 21, 1989.

[51] Int. Cl.⁵ .................. A61K 31/675; C07F 9/572; C07F 9/60; C07F 9/62
[52] U.S. Cl. .......................... 514/80; 514/82; 540/476; 540/542; 546/22; 546/23; 548/113; 548/414
[58] Field of Search ............... 548/414, 113; 546/23, 546/22; 540/476, 542; 514/80, 82

[56] References Cited

PUBLICATIONS

Karenewsky, J. Med. Chem. 33, 1459–1469 (1990).

*Primary Examiner*—Mark L. Berch
*Attorney, Agent, or Firm*—Timothy J. Gaul

[57] ABSTRACT

Hypotensive activity is exhibited by new phosphonate substituted amino or imino acids of the formula

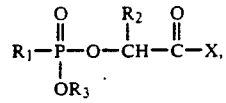

isomeric mixtures thereof and pharmaceutically acceptable salts thereof, wherein:

X is an imino or amino acid of the formula

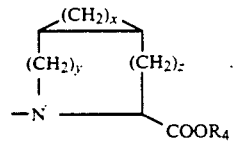

10 Claims, No Drawings

PHOSPHONATE SUBSTITUTED AMINO ACIDS USEFUL AS ANTIHYPERTENSIVES

This is a division of application Ser. No. 396,170, filed Aug. 21, 1989.

BRIEF DESCRIPTION OF THE INVENTION

This invention is directed to new phosphonate substituted amino or imino acids of the formula $$R_1-\overset{O}{\underset{OR_3}{\overset{\|}{P}}}-O-\overset{R_2}{\underset{}{\overset{|}{C}H}}-\overset{O}{\overset{\|}{C}}-X.$$

isomeric mixtures thereof and pharmaceutically acceptable salts thereof, wherein in formula I and throughout this specification, the symbols are defined as follows:

X is an imino or amino acid of the formula

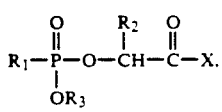

$R_1$ is alkyl of 1 to 10 carbons, aminoalkyl, haloalkyl,

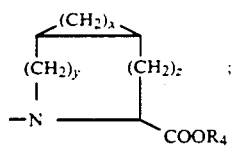

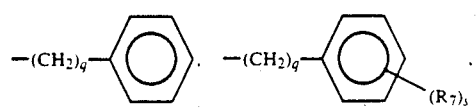

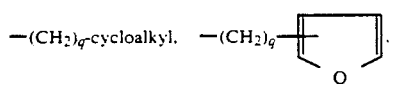

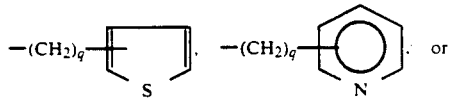

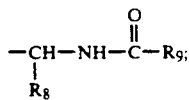

$R_2$ is hydrogen, lower alkyl, halo substituted lower alkyl,

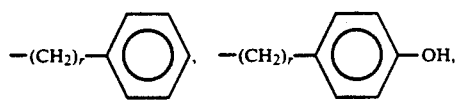

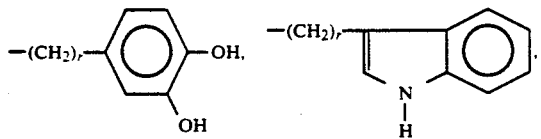

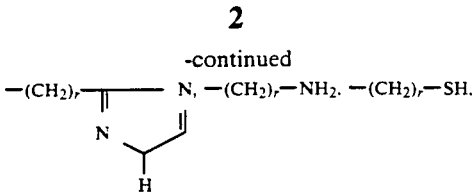

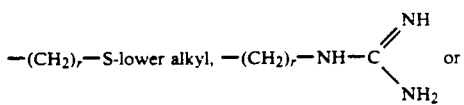

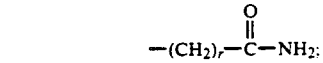

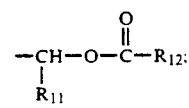

$R_3$ is independently selected from hydrogen, lower alkyl, benzyl, alkali metal such as Li, Na or K, benzhydryl, or

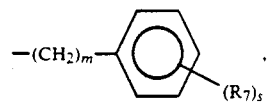

$R_7$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_8$ and $R_9$ are independently selected from hydrogen, lower alkyl, halo-substituted lower alkyl,

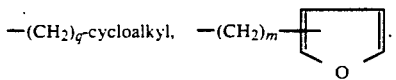

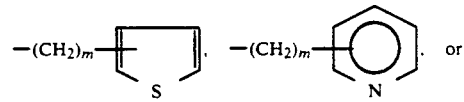

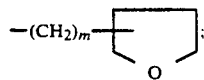

$R_{10}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

$R_{11}$ is hydrogen, lower alkyl, cycloalkyl, or phenyl, and $R_{12}$ is hydrogen, lower alkyl, lower alkoxy, phenyl, or $R_{11}$ and $R_{12}$ taken together are $-(CH_2)_2-$, $-(CH_2)_3-$, $-CH=CH-$, or

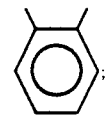

m is zero, one, two or three;

p is one, two or three, provided that p is more than one only if $R_{10}$ is hydrogen, methyl, methoxy, chloro, or fluoro;

q is an integer from 0 to 7;

r is an integer from 1 to 4;

s is one, two or three;

x is an integer from 1 to 4;

y is zero, one, or two; and z is zero, one, or two.

This invention in its broadest aspects relates to the phosphonate substituted imino or amino acid compounds of formula I above, to compositions containing such compounds and to the method of using such compounds as anti-hypertensive agents.

DEFINITION OF TERMS

The following definitions apply to the terms as they are used throughout this specification, unless otherwise limited in specific instances.

The term "alkyl" refers to straight or branched chain hydrocarbon groups having up to ten carbons, for example, methyl, ethyl, propyl, isopropyl, butyl, isobutyl, t-butyl, pentyl, isopentyl, heptyl, octyl, decyl, etc. The term "lower alkyl" refers to straight or branched chain groups having up to seven carbons. The preferred lower alkyl groups have up to four carbons with methyl and ethyl most preferred. Similarly, the terms "lower alkoxy" and "lower alkylthio" refer to such lower alkyl groups attached to an oxygen or sulfur.

The term "cycloalkyl" refers to saturated rings of 3 to 7 carbon atoms, with cyclopentyl and cyclohexyl being most preferred.

The terms "halo" and "halogen" refer to fluorine, chlorine, and bromine.

The term "halo-substituted lower alkyl" refers to such lower alkyl groups described above in which one or more hydrogens have been replaced by chloro, bromo or fluoro groups, such as trifluoromethyl (which is preferred) pentafluoroethyl, 2,2,2-trichloroethyl, chloromethyl, bromomethyl, etc. Similarly, the term "amino-substituted lower alkyl" refers to lower alkyl groups in which one or more hydrogens have been replaced by $-NH_2$, i.e., aminomethyl, 2-aminoethyl, etc.

The compounds of this invention wherein $R_3$ is hydrogen form basic salts with various inorganic and organic bases which are also within the scope of the invention. Such salts include ammonium salts, alkali metal salts such as lithium, sodium and potassium salts (which are preferred), alkaline earth metal salts such as calcium and magnesium salts, salts with organic bases (e.g., dicyclohexylamine salt), benzathine, N-methyl-D-glucamine, hydrabamine salts, and salts with amino acids such as arginine, lysine and the like. The nontoxic, physiologically acceptable salts are preferred, although other salts are also useful, for example, in isolating or purifying the products. The salts are formed using conventional techniques. All of the foregoing are within the meaning of the term "pharmaceutically acceptable salts."

The amino or imino acid or ester portion of the molecule of the products of formula I represented by X is in the L-configuration. Depending upon the definitions of $R_2$ and $R_8$, other asymmetric centers may be present in the phosphonyl sidechain. Thus, some of the compounds can exist in diastereoisomeric forms or in mixtures thereof. The above-described processes can utilize racemates, enantiomers or diastereomers as starting materials. When products containing only a single diastereomer are preferred, they can be separated by conventional chromatographic or fractional crystallization methods. The products of formula I wherein the imino acid ring is monosubstituted give rise to cis-trans isomerism. All of the foregoing are within the meaning of the term "isomeric mixtures."

PROCESS OF PREPARATION

The compounds of formula I wherein $R_1$ is other than

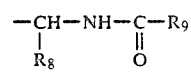

are prepared according to the following procedures. A phosphonic acid of formula

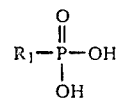

is treated with a chlorinating agent (e.g., phosphorus pentachloride) in the presence of an inert organic solvent (e.g., benzene) to form a compound of the formula

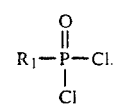

Compound III is reacted with a lactate of the formula

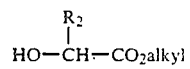

in the presence of an organic base (e.g., triethylamine) followed by an alcohol ROH (where $R_3$ is lower alkyl, benzyl, or benzhydryl) to form a compound of the formula

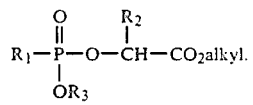

The formula V compound is then treated with strong base (e.g., sodium hydroxide or lithium hydroxide) in a mixture of water and an organic solvent (e.g., dioxane) to form the corresponding acid

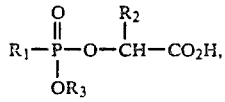

The acid VI or its activated form is then coupled with an imino or amino acid or ester of the formula VII

The term "activated form" refers to the conversion of the acid to a mixed anhydride, symmetrical anhydride, acid chloride, or activated ester; see *Methoden der Or-*

*ganischen Chemie* (Houben-Weyl), Vol. XV, part II, page 1 et seq. (1974) for a review of the methods of acylation. Preferably, the reaction is performed in the presence of a coupling agent such as 1,1-carbonyldiimidazole, thionyl chloride, or dicyclohexylcarbodiimide.

In the above reaction, if $R_2$ is

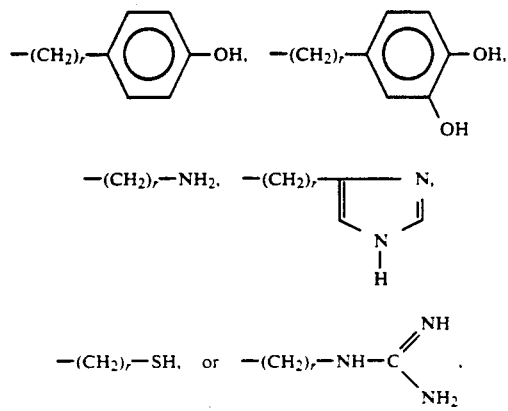

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Similarly, if in the above reaction $R_1$ is aminoalkyl, then the amino group should be similarly protected, preferably by phthalidyl. The protecting group is removed by treatment with hydrazine following completion of the reaction.

The products of formula I wherein $R_3$ is hydrogen can be derived by hydrogenating those products wherein $R_3$ is benzyl or benzhydryl. Such hydrogenation can be effected, for example, by treatment with hydrogen in the presence of a palladium on carbon catalyst. Products in which $R_3$ and/or $R_4$ are alkyl can be converted to products in which $R_3$ and $R_4$ are hydrogen by chemical treatment, such as with sodium hydroxide in aqueous dioxane or trimethylsilybromide in dichloromethane.

The ester products of formula I wherein $R_3$ is

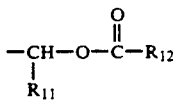

may be obtained by employing the imino or amino acid of formula V in the above reactions with the ester group already in place. Such ester reactants can be prepared by treating peptide, imino, or amino acids with an acid chloride such as

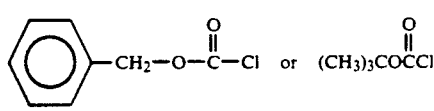

so as to protect the N-atom. The protected acid compound is then reacted in the presence of base with a compound of the formula

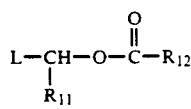

wherein L is a leaving group such as chlorine, bromine, tolysulfonyloxy, etc., followed by removal of N-protecting group (e.g., by treatment with acid or hydrogenation).

The various imino and amino acids and esters of formula V are described in the literature and in the various patents referred to above. Various substituted prolines are also disclosed by Mauger et al., *Chem. Review*, Vol. 66, p. 46–86 (1966). When the amino or imino acid is known, it can be readily converted to the ester by conventional means.

The compounds of formula I wherein $R_1$ is

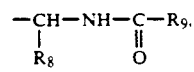

that is

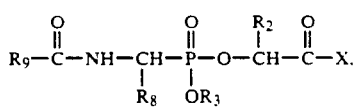

may be prepared by reacting an aminophosphonic acid of the formula

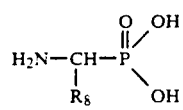

with an acid chloride having the formula

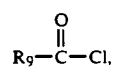

such as benzoyl chloride, in the presence of an inert organic solvent (e.g., dioxane) and a weak organic base (e.g., triethylamine) to yield

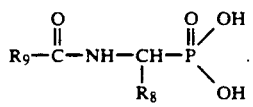

The formula XVI compound is then coupled with an imino or amino acid or ester of formula XVII

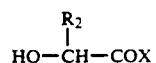

in the presence of a coupling agent (e.g., dicyclohexylcarbodiimide) as described above to form

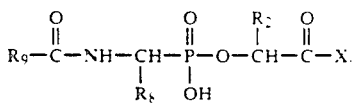   XVIII

Where X includes a protecting group, it may be removed by (1) hydrogenation where the protecting group is phenylmethoxycarbonyl or by (2) treatment with hydrazine where the protecting group is phthalidyl, to yield the compounds of formula XIII.

The compounds of formula XVII may be prepared by coupling a hydroxy acid of formula

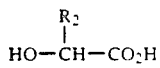   XIX as the free acid or corresponding sodium salt with an imino or amino ester of formula VII, preferably in the presence of a coupling agent such as diphenyl phosphorylazide.

PREFERRED MOIETIES

Preferred compounds of this invention with respect to the phosphonyl sidechain of the structure of formula I are those wherein:

$R_2$ is hydrogen, lower alkyl of 1 to 4 carbons, aminosubstituted lower alkyl, guanidinosubstituted lower alkyl or $CF_3$;

$R_3$ is hydrogen, an alkali metal salt, lower alkyl of 1 to 4 carbons, or

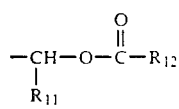

wherein $R_{11}$ is hydrogen, methyl or isopropyl and $R_{12}$ is hydrogen or straight or branched chain lower alkyl of 1 to 4 carbons or phenyl, especially hydrogen, alkali metal salt, ethyl,

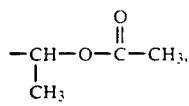

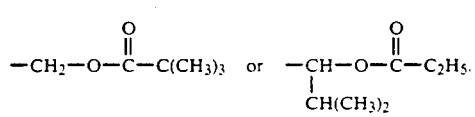

$R_1$ is alkyl of 1 to 10 carbons;

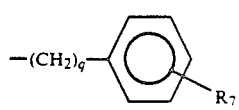

wherein q is an integer from 0 to 5 and $R_7$ is methyl, methoxy, methylthio, chloro, bromo, fluoro, or hydroxy; —$(CH_2)_q$— cycloalkyl wherein cycloalkyl is of 5 or 6 carbons and q is zero, one or two;

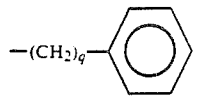

wherein q is an integer from 0 to 5;

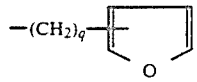

wherein q is an integer from 0 to 5;

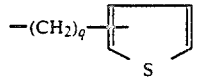

wherein q is an integer from 0 to 5;

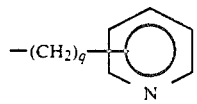

wherein q is an integer from 0 to 5; or

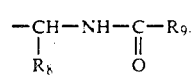

$R_8$ and $R_9$ are independently selected from lower alkyl of 1 to 4 carbons or

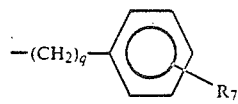

wherein q is an integer from 0 to 5 and $R_7$ is hydrogen, methyl, methoxy, methylthio, chloro, bromo, fluoro, or hydroxy, especially wherein $R_8$ is phenylethyl and $R_9$ is phenyl.

USE AND UTILITY

The compounds of formula I, and the pharmaceutically acceptable salts thereof, are hypotensive agents. They inhibit the conversion of the decapeptide angiotensin I to angiotensin II and, therefore, are useful in reducing or relieving angiotensin-related hypertension. The action of the enzyme renin on angiotensinogen, a psuedo-globulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensiongen→(renin)→angiotensin I→angiotensin II sequence by inhibiting angiotensin converting enzyme and reducing or eliminating the formation of the pressor substance angiotensin II. Thus, by the administration of a composition containing one (or a combination) of the compounds of this invention, angiotensin-dependent hypertension in a species of mammal (e.g., humans) suffering therefrom is alleviated. A single dose, or preferably two to four divided daily doses, provided on a basis of about 0.1 to 100 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dose of about 30 to 600 mg (preferably about 30 to 330 mg) of a compound of this invention, and about 15 to 300 mg (preferably about 15 to 200 mg) of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, tricynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with a physiologically acceptable vehicle, carrier, excipient, binder, preservatives, stabilizer, flavor, etc., in a unit dosage form as called for by accepted pharmaceutical practice. The amount of active substance in these compositions or preparations is such that a suitable dosage in the range indicated is obtained.

SPECIFIC EMBODIMENTS

The following working examples are illustrative and present preferred embodiments of the invention. Preparation of intermediate compounds appears just below the names of intermediate compounds. The intermediate prepared in part A of a working example will be referred to as "compound A" or "intermediate A" as a shorthand reference, and likewise for compounds prepared in parts B, C, D, etc. Except where otherwise indicated, all temperatures are in degrees Celsius.

EXAMPLE 1

[2S-[2α,3aβ,7aβ]]-1-[(S)-6-Amino-2-[[hydroxy(4-phenylbutyl)phosphinyl]oxy]-1-oxohexyl]octahydro-1H-indole-2-carboxylic acid, dilithium salt A. [2α,3aβ,7aβ]Octahydro-1H-indole-2-carboxylic acid, ethyl ester hydrochloride A mixture of ethyl(S)indoline-2-carboxylate hydrochloride (2.0 g, 8.8 mmole) and 10% palladium on charcoal (0.6 g) in 60 ml of absolute ethanol was hydrogenated overnight. The reaction was filtered through "Celite", rinsing with ethanol. The filtrate was concentrated in vacuo to a yellowish oil. The product was crystallized from ethyl acetate (60 ml). The product was collected and dried in vacuo to yield 1.3 g (63.5%) of intermediate A.

Melting point 138°–140° C. Lit. (139°–140° C.).

$[\alpha]_D = -27.2°$ (c=1.0, water) [Lit.$[\alpha]_D = -27.8°$ (c=1, water)].

Thin layer chromatography: [7:2:1 Isopropanol, ammonium hydroxide, water] Rf=0.55 PMA visualized.

B.
(S)-2-Hydroxy-6-[(phenylmethoxy)carbonyl]amino]-hexanoic acid

This compound was prepared as described in U.S. Pat. No. 4,616,005, Example 137, part B.

C.
[2S-[2α,3aβ,7aβ]]-1-[[(S)-2-Hydroxy-1-oxo-6-[(phenylmethoxy)carbonyl]amino]hexyl]-octahydro-1H-indole-2-carboxylic acid, ethyl ester A solution of intermediate B (1.20 g, 4.49 mmole), intermediate A (1.30 g, 5.56 mmole), and triethylamine (.072 ml, 5.17 mmole) in dry tetrahydrofuran (15 ml) was cooled to 0° C. under argon. 1,3 Dicyclohexylcarbodiimide (1.01 g, 4.90 mmole) and 1-hydroxybenzotriazole hydrate (0.66 g, 4.90 mmole) were added. The reaction was stirred at 0° C. for 3 hours and at room temperature for one hour. The reaction was diluted with ethyl acetate and filtered to remove dicyclohexylurea. The filtrate was washed with 5% potassium bisulfate (twice), saturated sodium bicarbonate, and brine, and dried over sodium sulfate. The solvent was removed in vacuo to yield 2.1 grams of oil, which was chromatographed on silica gel and eluted with hexanes:ethyl acetate (2:1) to yield 1.6 g (77.5%) of intermediate C.

$[\alpha]_D = -34.22°$ C. (c=1.73, ethanol).

Thin layer chromatography: (20:1:1) CH$_2$Cl$_2$: methanol:acetic acid.

R$_f$=0.6 PMA visualized.

D.
[2S-[2α,3aβ,7aβ]]-1-[(S)-2-[[hydroxy-(4-phenylbutyl)-phosphinyl]]oxy]-1-oxo-6-[(phenylmethoxy)carbonyl-]aminohexyl]-octahydro-1H-indole-2-carboxylic acid, ethyl ester To a solution of intermediate C (1.6 g, 3.48 mmole) and phenylbutylphosphonous acid (1.03 g, 5.2 mmoles) in dry tetrahydrofuran (20 ml) was added dicyclohexylcarbodiimide (1.07 g. 5.2 mmol) and dimethylaminopyridine (0.2 g). The reaction was stirred at room temperature for 2 hours. Additional phosphonous acid (0.5 g, 2.6 mmole) and dicyclohexylcarbodiimide (0.53 g, 2.6 mmole) were added. The reaction was stirred for 48 hours. The mixture was diluted with ethyl acetate and filtered. The filtrate was washed with 5% potassium bisulfate (twice), saturated sodium bicarbonate, brine, and dried over sodium sulfate. The solvent was removed in vacuo and the residue was dissolved in ethyl acetate:hexanes (1:1, filtered, and concentrated to yield 1.9 g of the coupled product.

Thin layer chromatography: (7:3) ethyl acetate: hexanes

R$_f$=0.2 (7:3) ethyl ether:acetone R$_f$=0.5.

The residue was dissolved in 25 ml dioxane and treated with a solution of sodium metaperiodate (0.96 g, 4.5 mmole) in 5 ml of water. The reaction was stirred overnight at room temperature then diluted with ethyl acetate. The organic phase was washed with 1% potassium bisulfate (twice), diluted with sodium bisulfate (twice), brine, and dried over sodium sulfate. The solvent was removed in vacuo and the residue was dissolved in diethyl ether (9 ml). A solution of 1-adamantanamine (0.55 g) in 2 ml of ether was then added. After stirring 15 minutes, hexanes were added to precipitate the adamantanamine salt. The mother liquor was decanted. The salt was triturated repeatedly with hexane, then partitioned between ethyl acetate and 1N hydrochloric acid. The organic phase was washed with brine and dried over sodium sulfate. The solvent was removed to yield 1.35 g of intermediate D.

The crude acid intermediate D was dissolved in sodium bicarbonate (250 ml). The aqueous phase was extracted with ethyl ether (five times) then acidified to pH 2 and extracted with ethyl acetate (four times). The combined extracts were washed with brine and dried over sodium sulfate. The solvent was removed in vacuo to yield 1.25 g (55%) of a yellow oil (intermediate B).

Thin layer chromatography: [(20:1:1) methylene chloride:methanol:acetic acid.
$R_f = 0.2$.

E.
[2S-[2α,3aβ,7aβ]]-1-[(S)-6-Amino-2-[[hydroxy(4-phenylbutyl)phosphinyl]]oxy]-1-oxohexyl]octahydro-1H-indole-2-carboxylic acid, ethyl ester A mixture of intermediate D (1.25 g, 1.90 mmole) and 10% palladium on charcoal (0.3 g) in absolute ethanol was hydrogenated at atmospheric pressure overnight. The catalyst was removed by filtration and the filtrate was concentrated in vacuo to yield 0.75 g [H908-008-1] of an oil. Thin layer chromatography [(7:2:1) isopropanol:ammonium hydroxide:water, $R_f = 0.7$] indicated two spots. Chromatography on HP-20, using a gradient system of acetonitrile: water gave purer product.

This product (0.30 g) was rechromatographed on HP-20 to yield 280 mg (28.2%) pure intermediate E.

F.
[2S-[2α,3aβ,7aβ]]-1-[(S)-6-Amino-2-[[hydroxy(4-phenylbutyl)phosphinyl]oxy]-1-oxohexyl]octahydro-1H-indole-2-carboxylic acid, dilithium salt A solution of intermediate E (280 mg, 0.536 mmole) in 5 ml of 1N lithium hydroxide and 4 ml of methanol was stirred at room temperature overnight. Saponification was judged completed by thin layer chromatography (7:2:1 isopropanol: ammonium hydroxide:water, $R_f = 0.35$). The reaction was concentrated in vacuo to remove methanol, and the aqueous solution was chromatographed on HP-20. The column was eluted with a gradient from 100% water to 50% water:acetonitrile. Fractions containing intermediate F were concentrated in vacuo. The resulting oil was dissolved in distilled water and filtered, then lyophilized to yield 0.21 g (81%) of Example 1.

EXAMPLE 2
[2S-[1(R*),2α,3aβ,6aβ]]-1-[6-Amino-2-[[hydroxy(4-phenylbutyl)phosphinyl]oxy]-1-oxohexyl]octahydrocyclopenta[β]pyrrole-2-carboxylic acid, dilithium salt

A.
[2α,3aβ,6aβ]-Octahydrocyclopenta[β]pyrrole-2-carboxylic acid, phenylmethyl ester The preparation of this compound is described in *Tetrahedron Letters*, Vol. 26, No. 15, pp. 1839–1842, by H. Urbach and R. Henning. A second equivalent of N-benzylglycine ethyl ester was used as base in the pyrrole synthesis rather than triethylamine. The compound was resolved as described in *Tetrahedron Letters*, Vol. 25, No. 40, pp. 4479–4482, by V. Teetz, R. Geiger and H. Gaul. $[\alpha]_D = -34.7$ (c=1.00, water) Lit. $[\alpha]_D = -38.4$.

B. (S)-6-[[(Phenylmethoxy)carbonyl)amino]-2-hydroxy heranoic acid

This compound was prepared as described in U.S. Pat. No. 4,616,005, Example 137, part B.

C.
[2S[1(R*),2α,3aβ,3aβ,6aβ]]-1-[[(S)-2-Hydroxy-1-oxo-6-[(phenylmethoxy)carbonyl]amino]hexyl]octahydrocyclopenta[β]pyrrole-2-carboxylic acid, phenylmethyl ester Intermediate compound A (434 mg, 1.54 mmol) and Intermediate compound B (434 mg, 1.54 mmol) were dissolved in 10 ml tetrahydrofuran and cooled to 0°. Triethylamine (0.31 ml, 0.22 g, 2.22 mmol), dicyclohexylcarbodiimide (340 mg, 1.65 mmol), and hydroxybenzotriazole (222 mg, 1.64 mmol) were added. The reaction mixture was stirred for two hours at 0°, warmed to room temperature and stirred an additional two hours. The [see 29,644] product was chromatographed on LPS-1 using 4:1 hexane:acetone.

Product-containing fractions were combined to give 550 mg (1.15 mmol, 75%) of compound C.

$^{13}$C NMR showed that this was contaminated with a small amount of the corresponding lactone.

Thin layer chromatography: (1:1 hexane:acetone) $R_f = 0.52$, with no sign of the less polar epimer.

D.
[2S-[1(R*),2α,3aβ,6aβ]]-1-[(S)-2-[[hydroxy-(4-phenylbutyl)phosphinyl]]oxy]-1-oxo-6-[(phenylmethoxy)carbonyl]aminohexyl]octahydrocyclopenta[β]pyrrole-2-carboxylic acid, phenylmethyl ester Intermediate compound C (550 mg, 1.15 mmol) and phenylbutylphosphonous acid (1.5 mmol, 296 mg) were dissolved in 10 ml tetrahydrofuran. Dicyclohexylcarbodiimide (309 mg, 1. mmol) and dimethylaminopyridine (50 mg) were added and the reaction stirred for four hours at room temperature. The intermediate phosphonous ester was oxidized to the phosphonic monoester with 340 mg sodium metaperiodate, [using reaction and workup conditions described in Example 9, part E] giving 730 mg (1.04 mmol, 90%) Intermediate D. Thin layer chromatography: $R_f = 0.23$ (20:1:1 methylene chloride:methanol:acetic acid).

E.
[2S-[1(R*),2α,3aβ,3aβ,6aβ]]-1-[6-Amino-2-[[hydroxy(4-phenylbutyl)phosphinyl]oxy]-1-oxohexyl]octahydrocyclopenta[β]pyrrole-2-carboxylic acid, dilithium salt Intermediate compound D (730 mg, 1.04 mmol) was dissolved in 50 ml methanol and stirred under atmospheric pressure hydrogen with 70 mg of Adams catalyst until uptake of hydrogen ceased. The solution was filtered through "Celite" and concentrated in vacuo. The product was not very water-soluble, so 1N lithium hydroxide was added to the compound in 20 ml water until the solution was basic. This solution was then loaded onto an HP-20 column, which was eluted with 1:1 water:acetonitrile gradient. Product-containing fractions were combined and concentrated, then dissolved in 25 ml water, filtered through a polycarbonate membrane, frozen and lyophilized. This gave 170 mg (0.33 mmol, 32%) of Example 2. $[\alpha]_D = -1.4$ (c=0.5, methanol).

Melting point 195°-200° C.

Electrophoresis (pH 9.2, 300 V, 90 minutes) B12 0.0 cm, Compound +2.4, NANOS+6.0, DPP−5.7.

C,H,N,P Analysis: calculated for $C_{24}H_{35}N_2O_6PLi_2$·water: Calculated: C,56.45; H,7.30; N,5.49; P,6.07. Found: C,56.45; H,7.49; N,5.62; P,5.8.

Thin layer chromatography (7:2:1 isopropanol:ammonium hydroxide:water) $R_f = 0.25$.

EXAMPLES 3 to 10

The following compounds were prepared by the methods used in Example 18.

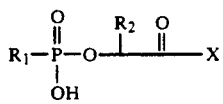

| No. | R₁ | R₂ | X |
|-----|----|----|---|
| 3. | ⟨furan⟩-(CH₂)₄— | —CH₃ | ⟨bicyclic N-COOH⟩ |
| 4. | Ph—(CH₂)₅— | —(CH₂)₄—NH₂ | ⟨bicyclic N-COOH⟩ |
| 5. | ⟨cyclohexyl⟩-(CH₂)₄— | —(CH₂)₃—NH₂ | ⟨bicyclic N-COOH⟩ |
| 6. | Ph—(CH₂)₄— | —(CH₂)₂—Ph | ⟨cyclopropane-fused N-COOH⟩ |
| 7. | ⟨4-pyridyl⟩-(CH₂)₄— | —(CH₂)₂—OH | ⟨bicyclic N-COOH⟩ |
| 8. | CH₃—(CH₂)₅— | —(CH₂)₃—CH₃ | ⟨bicyclic N-COOH⟩ |
| 9. | CH₃—(CH₂)₅— | —(CH₂)₃—NH₂ | ⟨bicyclic N-COOH⟩ |

| No. | R₁ | R₂ | X |
|---|---|---|---|
| 10. | CH₃—(CH₂)₅— | —(CH₂)₄—NH₂ | 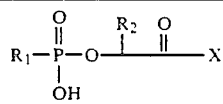 |

What is claimed is:

1. A compound of the formula

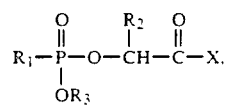

and pharmaceutically acceptable salts thereof, wherein:

X is

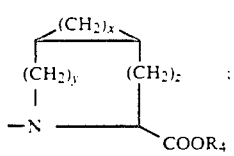

$R_1$ is alkyl of 1 to 10 carbons, aminoalkyl, haloalkyl,

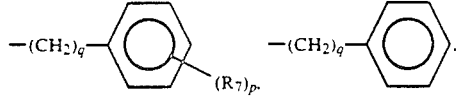

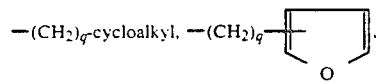

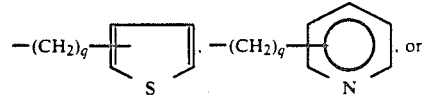

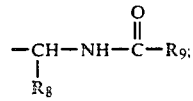

$R_2$ is hydrogen, lower alkyl, halo substituted lower alkyl,

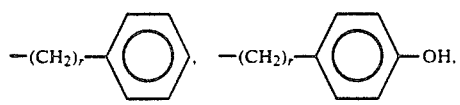

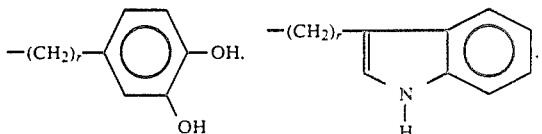

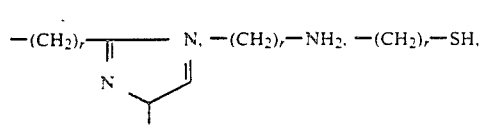

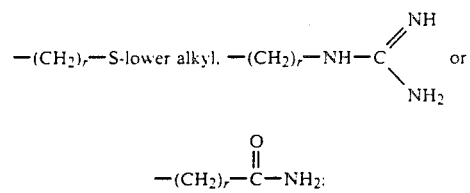

$R_3$ and $R_4$ are independently selected from hydrogen, lower alkyl, benzyl, alkali metal, benzhydryl, or

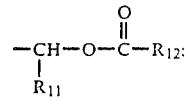

$R_7$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_8$ and $R_9$ are independently selected from hydrogen, lower alkyl, halo-substituted lower alkyl,

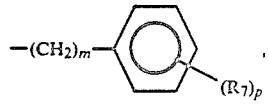

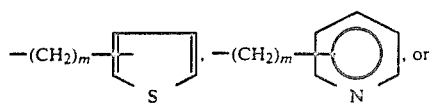

-continued

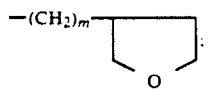

$R_{11}$ is hydrogen, lower alkyl, cycloalkyl, or phenyl, and $R_{12}$ is hydrogen, lower alkyl, lower alkoxy, phenyl, or $R_{11}$ and $R_{12}$ taken together are —(CH$_2$)$_2$—, —(CH$_2$)$_3$—, —CH=CH—, or

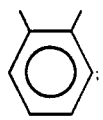

m is zero, one, two or three;

p is one, two or three, provided that p is more than one only if $R_7$ is hydrogen, methyl, methoxy, chloro, or fluoro;

q is an integer from zero to seven;

r is an integer from one to four;

x is an integer from one to four;

y is zero, one, or two; and z is zero, one, or two.

2. A compound of claim 1, wherein:
$R_4$ is hydrogen or alkali metal.

3. A composition useful for treating hypertension comprising a pharmaceutically acceptable carrier and an effective amount of a compound of claim 1.

4. A compound of claim 1, wherein:
$R_2$ is —(CH$_2$)$_r$—NH$_2$ wherein r is an integer from 1 to 4.

5. A compound of claim 1, wherein:
$R_3$ is hydrogen or alkali metal.

6. A compound of claim 1, wherein:
$R_1$ is

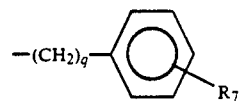

wherein q is an integer from 0 to 5 and $R_7$ is hydrogen, methyl, methoxy, methylthio, chloro, bromo, fluoro, or hydroxy.

7. The composition of claim 3 further comprising a diuretic.

8. A method of alleviating hypertension in a mammalian species which comprises administering an effective amount of the compound of claim 1.

9. The compound of claim 1, [2S-[2α,3aβ,7aβ]]-1-[(S)-6-Amino-2-[[hydroxy-(4-phenylbutyl)phosphinyl]oxy]-1-oxohexyl]-octahydro-1H-indole-2-carboxylic acid, dilithium salt.

10. The compound of claim 1, [2S-[1(R*), 2α, 3aβ,6aβ]]-1-[6-Amino-2-[[hydroxy(4-phenylbutyl)phosphinyl]oxy]-1-oxohexyl]-octahydrocyclopenta[β]pyrrole-2-carboxylic acid, dilithium salt.

* * * * *